(12) United States Patent
Suslick et al.

(10) Patent No.: US 6,368,558 B1
(45) Date of Patent: Apr. 9, 2002

(54) COLORIMETRIC ARTIFICIAL NOSE HAVING AN ARRAY OF DYES AND METHOD FOR ARTIFICIAL OLFACTION

(75) Inventors: Kenneth S. Suslick; Neal A. Rakow, both of Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/532,125

(22) Filed: Mar. 21, 2000

(51) Int. Cl.[7] ............................................. G01N 21/00
(52) U.S. Cl. ..................... 422/55; 422/68.1; 422/82.05; 422/83; 422/85; 436/164; 436/172
(58) Field of Search ..................... 422/55, 68.1, 82.05, 422/82.06, 82.07, 82.08, 82.09, 82.11, 83, 85; 436/164, 165, 172

(56) References Cited

U.S. PATENT DOCUMENTS

| | | | |
|---|---|---|---|
| 4,759,210 A | | 7/1988 | Wohltjen |
| 4,907,441 A | | 3/1990 | Shurmer |
| 5,489,988 A | * | 2/1996 | Ackley et al. ............... 356/436 |
| 5,512,490 A | | 4/1996 | Walt et al. |
| 5,733,506 A | | 3/1998 | Silver |
| 5,786,219 A | * | 7/1998 | Zhang et al. ................ 436/523 |
| 5,814,524 A | * | 9/1998 | Walt et al. ................... 436/518 |
| 5,863,460 A | | 1/1999 | Slovacek et al. |
| 5,952,237 A | | 9/1999 | Tanaka et al. |
| 5,955,603 A | | 9/1999 | Therien |
| 5,994,150 A | * | 11/1999 | Challener et al. ........... 436/518 |
| 6,078,705 A | * | 6/2000 | Neuschafer et al. .......... 385/12 |
| 6,140,138 A | | 10/2000 | Bard |

OTHER PUBLICATIONS

Krishna Persaud & George Dodd, "Analysis of Discrimination Mechanisms in the Mammalian Olfactory System using a Model Nose," Nature vol. 299, Sep. 23, 1982, pp. 352–355.

Janet Kavandi, James Callis, Martin Gouterman, Gamai Khalil, Daniel Wright, "Luminescent Barometry in Wind Tunnels," *Rev. Sci. Instrum,* vol. 61, No. 11, Nov., 1990, pp. 3340–3347.

Jay W. Grate and Michael H. Abraham, "Solubility Interactions and the Design of Chemically Selective Sorbent Coatings for Chemical Sensors and Arrays," *Sensors and Actuators,* B, 3 (1991) pp. 85–111.

Julian W. Gardner, Harold V. Shurmer and Paul Corcoran, "Integrated Tin Oxide Odour Sensors," *Sensors and Actuators* B, 4 (1991) pp. 117–121.

J.W. Gardner, H. V. Shurmer, and T. T. Tan, "Application of an Electronic Nose to the Discrimination of Coffees," *Sensors and Actuators* B, 6 (1992) pp. 71–75.

(List continued on next page.)

*Primary Examiner*—Jill Warden
*Assistant Examiner*—Dwayne K Handy
(74) *Attorney, Agent, or Firm*—Banner & Witcoff, Ltd.

(57) ABSTRACT

The present invention involves an artificial nose having an array comprising at least a first dye and a second dye in combination and having a distinct spectral response to an analyte. In one embodiment, the first and second dyes are from the group comprising porphyrin, chlorin, chlorophyll, phthalocyanine, or salen. In a further embodiment, the first and second dyes are metalloporphyrins. The present invention is particularly useful in detecting metal ligating vapors. Further, the array of the present invention can be connected to a visual display device.

35 Claims, 12 Drawing Sheets

(8 of 12 Drawing Sheet(s) Filed in Color)

OTHER PUBLICATIONS

Alan B. Baron, J.D.S. Danielson, Martin Gouterman, Jiang River Wan, "Submillisecond Response Times of Oxygen–Quenched Luminescent Coatings,"*Rev. Sci. Instrum.* 64 (12) Dec. 1993, pp. 3394–3402.

Weekey Wai–San Lee, Kwok–Yin Wong, Xiang–Ming Li, Yiu–Bong Leung, Chi–Shing Chan and Kin Shing Chan, Halogenated Platinum Porphyrins as Sensing Materials for Luminescence–Based Oxygen Sensors, *J. Mater Chem.* 1993, pp. 1031–1035.

Julian W. Gardner and Philip N. Bartlett, "A Brief History of Electronic Noses," *Sensors and Actuators* B, 18–19 (1994), pp. 211–220.

Michael S. Freund and Nathan S. Lewis, "A Chemically Diverse Conducting Polymer–Based Electronic Nose," *Proc. Natl. Acad. Sci. USA,* Mar. 1995, vol. 92, pp. 2652–2656.

Andrea E. Hoyt and Antonio J. Riccio, "Speciation of Linear and Branched Hydrocarbons by a Fluorinated Polyimide–Film–Based Surface Acoustic Wave Sensor," *J. Am. Chem. Soc.* 1995, 117, pp. 8672–8673.

Todd A. Dickinson, Joel White, John S. Kauer and David R. Walt, "A Chemical–Detecting System Based on a Cross–Reactive Optical Sensory Array," *Nature,* vol. 382, Aug. 22, 1996, pp. 697–700.

Andrew A. Vaughan, Mark G. Baron and Ramaier Narayanaswamy, "Optical Ammonia Sensing Films Based on an Immobilized Metalloporphyrin," *Analytical Communications,* Nov. 1996, vol. 33, pp. 393–396.

J.A.J. Brunink, et al., "The Application of Metalloporphyrins as Coating Material for Quartz Microbalance–Based Chemical Sensors," *Analytica Chimica ACTA,* 325 (1996) pp. 53–64.

Brett J. Doleman, Robert D. Sanner, Erik J. Severin, Robert H. Grubbs, and Nathan S. Lewis, "Use of Compatible Polymer Blends to Fabricate Arrays of Carbon Black–Polymer Composite Vapor Detectors,"*Analytical Chemistry,* vol. 70, No. 13, Jul. 1, 1998, pp. 2560–2564.

Richard M. Crooks and Antonio J. Ricco, "New Organic Materials Suitable for Use in Chemical Sensor Arrays," *Accounts of Chemical Research,* vol. 31, No. 5, 1998, pp. 219–227.

Gregory A. Sotzing, Jennifer N. Phend, Robert H. Grubbs and Nathan S. Lewis, "Highly Sensitive Detection and Discrimination of Biogenic Amines Utilizing Arrays of Polyaniline/Carbon Black Composite Vapor Detectors," *Chem. Mater.* 2000, vol. 12, published on Web Feb. 29, 2000, pp. 593–595.

Todd A. Dickinson, Karri L. Michael, John S. Kauer and David R. Walt, "Convergent, Self–Encoded Bead Sensor Arrays in the Design of an Artificial Nose," *Anal. Chem.* 1999, vol. 71, Jun. 1, 1999, pp. 2192–2198.

M.G. Baron, R. Narayanaswamy, S.C. Thorpe, "Hydrophobic Membrane Sensors for the Optical Determination of Hydrogen Chloride Gas," *Sensors and Actuators* B 34 (1996), pp. 511–515.

Abstract, Tanaka et al., "Gas–Sensitive Colorants, Gas Sensors and Apparatus and Method for Detecting Gas," Copyright 1999 ACS.

Suslick, K. S. & Van Deusen–Jeffries, S. in "Comprehensive Supramolecular Chemistry" (ed. Lehn, J.M.) 141–170 (Elsevier Science, Ltd., Oxford, 1996).

Adler, A. D. et al. "A Simplified Synthesis for meso–Tetraphenylporphin," *J. Org. Chem.* 32, 476 (1967).

Sen, A. & Suslick, K.S. "Shape Selective Discrimination of Small Organic Molecules," *J. Am. Chem. Soc.,* 1–9, p. S.1 and 2 (In the press).

Chou, J.–H., Nalwa, H.S., Kosal, M. E., Rakow, N.A. & Suslick, K.S., "Applications of Porphyrins and Metalloporphyrins to Materials Chemistry," From *The Porphyrin Handbook* (eds. Kadish, K., Smith, K., & Guilard, R.) p.43–132 (Academic Press, New York, 2000).

Heilig, A. et al., "Gas Identification of Modulating Temperatures of $SnO_2$–Based Thick Film Sensors," Sensor and Actuators B 43, 45–51 (1997).

Bhyrappa, P., Vaijayanthimala, G. & Suslick, K.S. "Shape––Selective Ligation to Dendrimer–Metalloporphyrins," *J. Am. Chem. Soc.* 121, 262–263 (1999).

Bhyrappa, P., Young, J.K., Moore, J.S. and Suslick, K.S. "Dendrimer–Metalloporphyrins: Synthesis and Catalysis," *J. Am. Chem. Soc.* 118, 5708–5711 (1996).

Datta–Gupta, N. & Bardos, T.J. "Synthetic Porphyrins II: Preparation and Spectra of Some Metal Chelates of para–Substituted–meso–Tetraphenylporphines," *J. Pharm. Sci.* 57, 300–304 (1968).

Nappa, M. & Valentine, J.S. "The Influence of Axial Ligands on Metalloporphyrin Visible Absorption Spectra. Complexes of Tetraphenylporphinatozinc," *J. Am. Chem. Soc.* 100, 5075–5080 (1978).

Barley, M., Becker, J. Y., Domazetis, G., Dolphin, D. & James, B. R. "Synthesis and Redox Chemistry of Octaethylporphyrin Complexes of Ruthenium (II) and Ruthenium (eIII)", *Can. J. Chem.,* 61, 2389–2396 (1983).

Adler, A. D., Long, F. R., Kampas, F. & Kim, J. "On the Preparation of Metalloporphyrins," *J. Inorg. Nucl. Chem.* 32, 2443–2445 (1970).

Di Natale, C. et al., "The Exploitation of Metalloporphyrins as Chemically Interactive Material in Chemical Sensors," *Materials Science & Engineering* C5, 209–215 (1998).

Walt, D. R. "Fiber Optic Imaging Sensors,"*Acc. Chem. Res.* 31, 267–278 (1998).

Lonergan, M.C. et al., "Array–Based Vapor Sensing Using Chemically Sensitive, Carbon Black–Polymer Resistors," *Chem. Mater.* 8, 2298–2312 (1996).

Axel, R. "The Molecular Logic of Smell," *Science Am.* 273, 154–159 (1995).

Lancet, D. & Ben–Arie, N. "Olfactory Receptors," *Curr. Biol.* 3, 668–674 (1993).

Dryer, L. & Berghard A. "Odorant Receptors: A Plethora of G–Protein–Coupled Receptors," *Trends Pharmacol. Sci.* 20, 413–417 (1999).

Gelperin, A., Flores, J., Raccuia–Behling, F., Cooke, I.R.C., "Nitric Oxide and Carbon Monoxide Modulate Oscillations of Olfactory Interneurons in a Terrestrial Mollusk," *J. Neurophysiol.* 83, 116–127 (2000).

Holten, D., and Gouterman, M., "Transient Absorption Spectra and Excited State Kinetics of Transitional Metal Porphyrins," *Optical Properties and Structure of Tetrapyrroles,* pp. 63–90 (Blauer, G. & Sund, H. (eds), Walter de Gruyter & Co., Berlin, 1985).

Yaws, C. L. Handbook of Vipor Pressure (Gulf, Houston, 1994), copy not enclosed.

\* cited by examiner

M(TPP)

| Metal | Z/r Ratio (Å⁻¹) |
|---|---|
| $Sn^{4+}$ | 5.80 |
| $Co^{3+}$ | 5.50 |
| $Cr^{3+}$ | 4.88 |
| $Mn^{3+}$ | 4.65 |
| $Fe^{3+}$ | 4.65 |
| $Co^{2+}$ | 3.08 |
| $Cu^{2+}$ | 2.74 |
| $Ru^{2+}$ | 2.71 |
| $Zn^{2+}$ | 2.70 |
| $Ag^{2+}$ | 2.13 |

$Sn^{4+}$  $Co^{3+}$  $Cr^{3+}$ $Mn^{3+}$  $Fe^{3+}$  $Co^{2+}$ $Cu^{2+}$  $Ru^{2+}$  $Zn^{2+}$ $Ag^{2+}$  $2H^+$
(FB)

US 6,368,558 B1

COLORIMETRIC ARTIFICIAL NOSE HAVING AN ARRAY OF DYES AND METHOD FOR ARTIFICIAL OLFACTION

This invention was made with Government support under Contract Nos. HL25934 awarded by the National Institutes of Health & Contract No. DAAG55-97-1-2211 awarded by the Department of the Army. The Government has certain rights in the invention.

FIELD OF THE INVENTION

The present invention relates to methods and apparatus for artificial olfaction, e.g., artificial noses, for the detection of odorants by a visual display.

BACKGROUND OF THE INVENTION

There is a great need for olfactory or vapor-selective detectors (i.e., "artificial noses") in a wide variety of applications. For example, there is a need for artificial noses that can detect low levels of odorants and/or where odorants may be harmful to humans, animals or plants. Artificial noses that can detect many different chemicals are desirable for personal dosimeters in order to detect the type and amount of odorants exposed to a human, the presence of chemical poisons or toxins, the spoilage in foods, the presence of flavorings, or the presence of vapor emitting items, such as plant materials, fruits and vegetables, e.g., at customs portals.

Conventional artificial noses have severe limitations and disadvantages and are not considered generally useful for such purposes. Limitations and disadvantages of conventional artificial noses include their need for extensive signal transduction hardware, and their inability to selectively target metal-coordinating vapors and toxins. In addition, artificial noses which incorporate mass sensitive signal transduction or polar polymers as sensor elements are susceptible to interference by water vapor. This limitation is significant in that it can cause variable response of the detector with changes ambient humidity. See F. L. Dickert, O. Hayden, Zenkel, M. E. *Anal. Chem.* 71, 1338 (1999).

Initial work in the field of artificial noses was conducted by Wilkens and Hatman in 1964, though the bulk of research done in this area.has been carried out since the early 1980's. See, e.g., W. F. Wilkens, A. D. Hatman. *Ann. NY Acad. Sci.*, 116, 608 (1964); K. Pursaud, G. H. Dodd. *Nature*, 299, 352–355 (1982); and J. W. Gardner, P. N. Bartlett. *Sensors and Actuators B*, 18–19, 211–220 (1994).

Vapor-selective detectors or "artificial noses" are typically based upon the production of an interpretable signal or display upon exposure to a vapor emitting substance or odorant (hereinafter sometimes referred to as an "analyte"). More specifically, typical artificial noses are based upon selective chemical binding or an interface between a detecting compound of the artificial nose and an analyte or odorant, and then transforming that chemical binding into a signal or display, i.e., signal transduction.

Polymer arrays having a single dye have been used for artificial noses. That is, a series of chemically-diverse polymers or polymer blends are chosen so that their composite response distinguishes a given odorant or analyte from others. Examples of polymer array vapor detectors, including conductive polymer and conductive polymer/carbon black composites, are discussed in: M. S. Freund, N. S. Lewis, *Proc. Natl. Acad. Sci. USA* 92, 2652–2656 (1995); B. J. Doleman, R. D. Sanner, E. J. Severin, R. H. Grubbs, N. S. Lewis, *Anal. Chem.* 70, 2560–2564 (1998); T. A. Dickinson, J. White, J. S. Kauer, D. R. Walt, *Nature* 382, 697–700 (1996)(polymer array with optical detection); A. E. Hoyt, A. J. Ricco, H. C. Yang, R. M. Crooks, *J. Am. Chem. Soc.* 117, 8672 (1995); and J. W. Grate, M. H. Abraham, *Sensors and Actuators B* 3, 85–111 (1991).

Other interface materials include fimctionalized self-assembled monolayers (SAM), metal oxides, and dendrimers. Signal transduction is commonly achieved with mass sensitive piezoelectric substrates, surface acoustic wave (SAW) transducers, or conductive materials. Optical transducers (based on absorbance or luminescence) have also been examined. Examples of metal oxide, SAM, and dendrimer-based detectors are discussed in J. W. Gardner, H. V. Shurner, P. Corcoran, *Sensors and Actuators B* 4, 117–121 (1991); J. W. Gardner, H. V. Shunner, T. T. Tan, *Sensors and Actuators B* 6, 71–75 (1992); and R. M. Crooks, A. J. Ricco, *Acc. Chem. Res.* 31, 219–227 (1998). These devices also use a single dye.

Techniques have also been developed using a metalloporphyrin for optical detection of a specific, single gas such as oxygen or ammonia, and for vapor detection by chemically interactive layers on quartz crystal microbalances. See A. E. Baron, J. D. S. Danielson, M. Gouterman, J. R. Wan, J. B. Callis, *Rev. Sci. Instrum.* 64, 3394–3402 (1993); J. Kavandi, et al., *Rev. Sci. Instrum.* 61, 3340–3347 (1990); W. Lee, et al.,*J. Mater. Chem.* 3, 1031–1035 (1993); A. A. Vaughan, M. G. Baron, R. Narayanaswamy, *Anal. Comm.* 33, 393–396 (1996); J. A. J. Brunink, et al.,*Anal. Chim. Acta* 325, 53–64 (1996); C. Di Natale, et al., *Sensors and Actuators B* 44, 521–526 (1997); and C. Di Natale, et al., *Mat. Sci. Eng. C* 5, 209–215 (1998). However, these techniques either require extensive signal transduction hardware, or, as noted above, are limited to the detection of a specific, single gas. They are also subject to water vapor interference problems, as discussed previously.

While typical systems to date have demonstrated some success in chemical vapor detection and differentiation, these systems have focused on the detection of non-metal binding or non-metal ligating solvent vapors, such as arenes, halocarbons and ketones. Detection of metal-ligating vapors (such as amines, thiols, and phosphines) has been much less explored. Further, while some single porphyrin based sensors have been used for detection of a single strong acid, there is a need for sensor devices that will detect a wide variety of vapors.

To summarize, there are a number of limitations and drawbacks to typical artificial noses and single porphyrin based sensors. As noted above typical artificial noses are not designed for metal binding and metal ligating vapors, such as amines, thiols, and phosphines. Further, typical artificial noses require extensive signal transduction hardware, and are subject to interference from water vapor. As noted above, single porphyrin based sensors have been used for detection of a single strong acid, but cannot detect a wide variety of vapors. Thus, there is a need for new artificial noses and methods that overcome these and other limitations of prior artificial noses and single porphyrin based sensors and methods.

SUMMARY OF THE INVENTION

The present invention comprises an array of dyes including at least a first dye and a second dye which in combination provide a spectral response distinct to an analyte or odorant. The dyes of the present invention produce a response in the spectrum range of about 200 nanometers to 2,000 nanometers, which includes the visible spectrum of light. It has now been discovered that an array of two or more dyes responds to a given ligating species with a unique color pattern spectrally and in a time dependent manner. Thus, dyes in the array of the present invention are capable of changing color in a distinct manner when exposed to any one analyte or odorant. The pattern of colors manifested by the multiple dyes is indicative of a specific or given analyte. In other words, the pattern of dye colors observed is indicative of a particular vapor or liquid species.

In a preferred embodiment, the dyes of the array are porphyrins In another preferred embodiment, the porphyrin dyes are metalloporphyrins. In a further preferred embodiment, the array will comprise ten to fifteen distinct metalloporphyrins in combination. Metalloporphyrins are preferable dyes in the present invention because they can coordinate metal-ligating vapors through open axial coordination sites, and they produce large spectral shifts upon binding of or interaction with metal-ligating vapors. In addition, porphyrins, metalloporphyrins, and many dyes show significant color changes upon changes in the polarity of their environment; this so-called solvatochromic effect will give net color changes even in the absence of direct bonding between the vapor molecules and the metal ions. Thus, metalloporphyrins produce intense and distinctive changes in coloration upon ligand binding with metal ligating vapors.

The present invention provides a means for the detection or differentiation and quantitative measurement of a wide range of ligand vapors, such as amines, alcohols, and thiols. Further, the color data obtained using the arrays of the present innovation may be used to give a qualitative fingerprint of an analyte, or may be quantitatively analyzed to allow for automated pattern recognition and/or determination of analyte concentration. Because porphyrins also exhibit wavelength and intensity changes in their absorption bands with varying solvent polarity, weakly ligating vapors (e.g., arenes, halocarbons, or ketones) are also differentiable.

Diversity within the metalloporphyrin array may be obtained by variation of the parent porphyrin, the porphyrin metal center, or the peripheral porphyrin substituents. The parent porphyrin is also referred to as a free base ("FB") porphyrin, which has two central nitrogen atoms protonated (i.e., hydrogen cations bonded to two of the central pyrrole nitrogen atoms). A preferred parent porphyrin is depicted in FIG. 2A, with the substitution of a two hydrogen ion for the metal ion (depicted as "M") in the center of the porphyrin. In FIG. 2A, TTP stands for 5,10,15,20-tetraphenylporphyrinate(-2).

In accordance with the present invention, colorimetric difference maps can be generated by subtracting unexposed and exposed metalloporphyrin array images (obtained, for example, with a common flatbed scanner or inexpensive video or charge coupled device ("CCD") detector) with image analysis software. This eliminates the need for extensive and expensive signal transduction hardware associated with previous techniques (e.g., piezoelectric or semiconductor sensors). By simply differencing images of the array before and after exposure to analytes, the present invention provides unique color change signatures for the analytes, for both qualitative recognition and quantitative analysis.

Sensor plates which incorporate vapor sensitive combinations of dyes comprise an embodiment of the present invention which is economical, disposable, and can be utilized to provide qualitative and/or quantitative identification of an analyte. In accordance with the present invention, a catalog of arrays and the resultant visual pattern for each analyte can be coded and placed in a look-up table or book for future reference. Thus, the present invention includes a method of detecting an analyte comprising the steps of forming an array of at least a first dye and a second dye, subjecting the array to an analyte, inspecting the first and second dyes for a spectral response, and comparing the spectral response with a catalog of analyte spectral responses to identify the analyte.

Because sensing is based upon either covalent interaction (i.e., ligation) or non-covalent solvation interactions between the analyte and the porphyrin array, a broad spectrum of chemical species is differentiable. While long response times (e.g., about 45 minutes) are observed at low analyte concentrations of about 1 ppm with reverse phase silica gel plates, use of impermeable solid supports (such as polymer- or glass-based micro-array plates) substantially increases the low-level response to about 5 minutes.

Thus, it is an object of the present invention to provide methods and devices for artificial olfaction, vapor-selective detectors or artificial noses for a wide variety of applications. It is another object of the present invention to provide methods of detection and artificial noses that can detect low levels of odorants and/or where odorants may be harmful to living human, animal or plant cells. It is also an object of the present invention to provide methods of olfactory detection and artificial noses that can detect and quantify many different chemicals for dosimeters that can detect chemical poisons or toxins, that can detect spoilage in foods, that can detect flavorings and additives, and that can detect plant materials, e.g., fruits and vegetables.

Another object of the present invention is to provide for the detection of analytes using data analysis/pattern recognition techniques, including automated techniques.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

DETAILED DESCRIPTION OF THE PREFERRED EMBODIMENTS

Production of The Sensor Plate of the Present Invention

Figure 1:
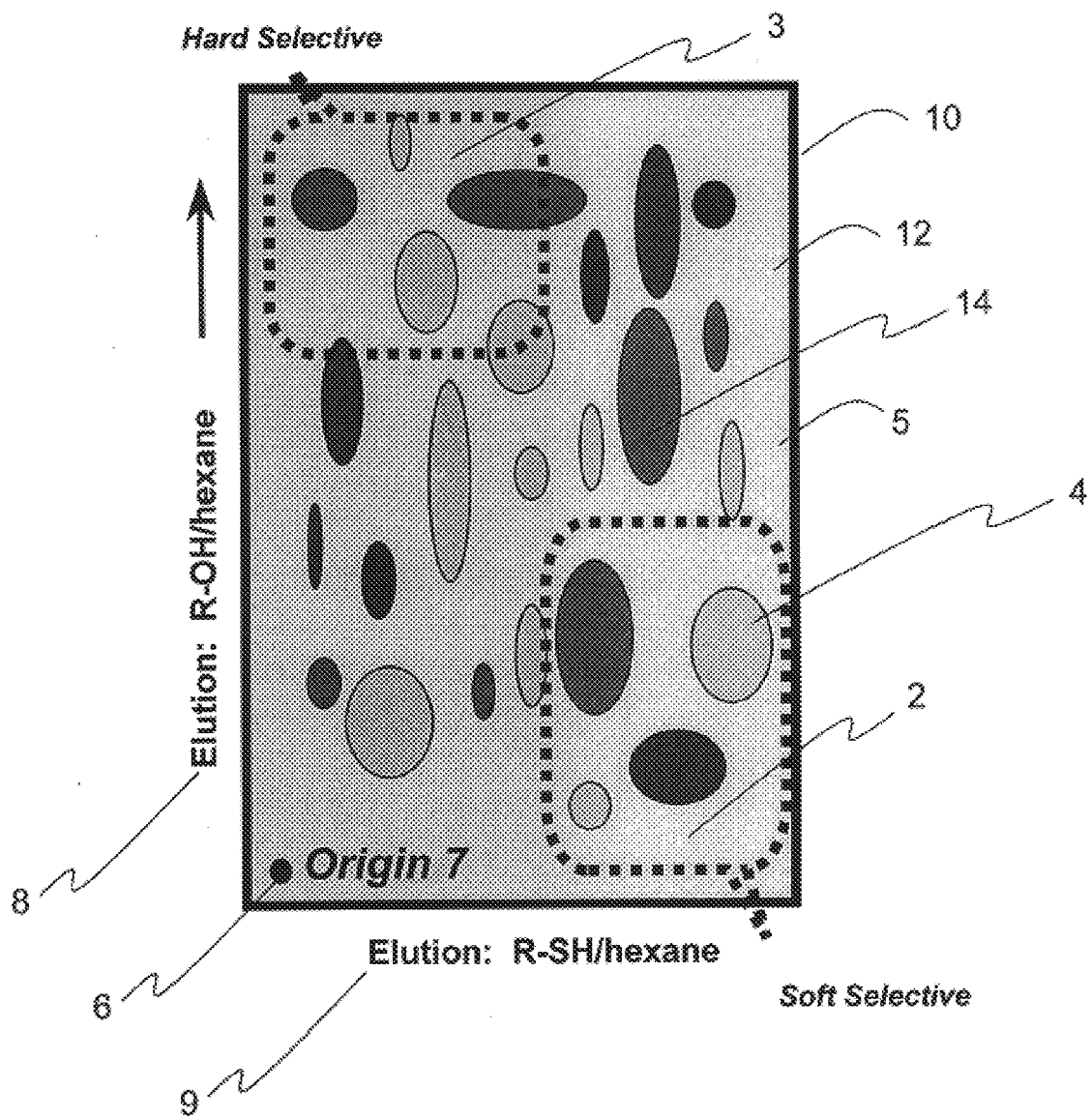
FIG. 1 illustrates an embodiment of the optical sensing plate of the present invention using a first elution in the y axis and a second elution in the x axis of the plate. In this embodiment the first elution R—OH/hexane and the second elution is R—SH/hexane.

A sensor plate 10 fabricated in accordance with the present invention is shown in FIG. 1. Sensor plate 10 comprises a two-dimensionally spatially resolved array 12 of various sensing elements or dyes 14 capable of changing color upon interaction (e.g., binding, pi-pi complexation, or polarity induced shifts in color). As shown in FIG. 1, a library of such dyes 14 can be given spatial resolution by two-dimensional chromatography or by direct deposition, including, but not limited to, ink-jet printing, micropipette spotting, screen printing, or stamping. In FIG. 1, metalloporphyrin mixture 6 is placed at origin 7. Next, the metalloporphyrin mixture 6 is eluted through a silica gel or reversed-phase silica gel 5 in sensor plate 10, and the metalloporphyrins are spatially resolved from each other and immobilized in silica gel 5 as depicted by the oval and circular shapes 4 as shown in FIG. 1. Sensor plate 10 can be made from any suitable material or materials, including but not limited to, chromatography plates, paper, filter papers, porous membranes, or properly machined polymers, glasses, or metals.

FIG. 1 also illustrates an embodiment of the optical sensing plate of the present invention using a first elution 8 in the y axis and a second elution 9 in the x axis of sensor plate 10. In this embodiment, the first elution 8 is R—OH/hexane and the second elution 9 is R—SH/hexane. The order of the first and second elutions can be reversed. The first and second elutions are used to spatially resolve the metalloporphyrin mixture 6 in silica gel 5. As shown in FIG. 1, the upper left hand quadrant 3 is characterized by metalloporphyrins that are "hard" selective, i.e., having a metal center mini having a high chemical hardness, i.e., a high charge density. As shown in FIG. 1, the lower right hand quadrant 2 is characterized by metalloporphyrins that are "soft" selective, i.e., having a metal center having a low chemical hardness, i.e., a low charge density. In accordance with the present invention, the array can be a spatially resolved collection of dyes, and more particularly a spatially resolved combinatorial family of dyes.

In accordance with the present invention, a porphyrin—metalloporphyrin sensor plate was prepared and then used to detect various odorants. More specifically, solutions of various metalated tetraphenylporphyrins in either methylene chloride or chlorobenzene were spotted in 1 μL aliquots onto two carbon ("C2", i.e, ethyl-capped) reverse phase silica thin layer chromatography plates product No. 4809-800, by Whatman, Inc., Clifton, N.J.) to yield the sensor array 16 seen in FIG. 2B. As shown in FIG. 2B and summarized in Table 1 below, the dyes have the following colors (the exact colors depend, among other things, upon scanner settings).

TABLE 1

| (Summarizing Colors of Dyes in FIG. 2B) | | |
| --- | --- | --- |
| $Sn^{4+}$ -- Green | $Co^{3+}$ -- Red | $Cr^{3+}$ -- Deep Green |
| $Mn^{3+}$ -- Green | $Fe^{3+}$ -- Dark Red | $Co^{2+}$ -- Red |
| $Cu^{2+}$ -- Red | $Ru^{2+}$ -- Light Yellow | $Zn^{2+}$ -- Greenish Red |
| $Ag^{2+}$ -- Red | $2H^+$ (Free Base "FB") - Red | |

Figure 2A:
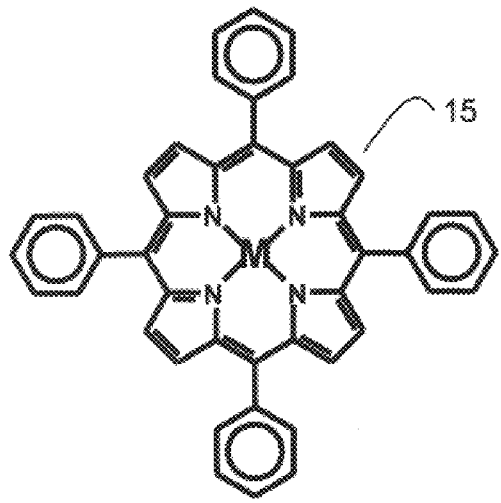
FIG. 2A illustrates an embodiment of the invention using metalloporphyrins as the sensing dyes.
Figure 2B:
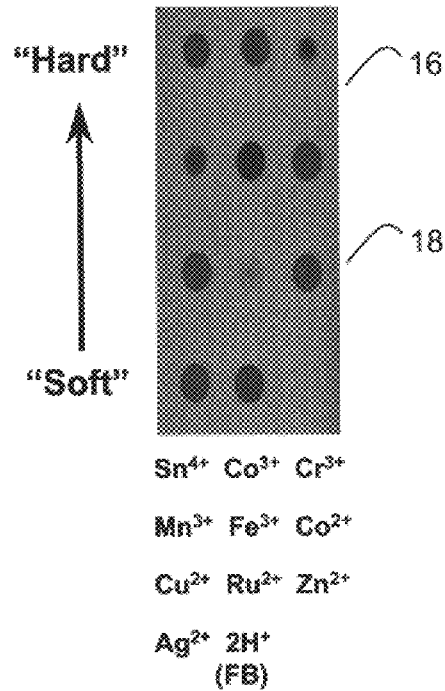
FIG. 2B illustrates an embodiment of the invention using metalloporphyrins as the sensing dyes.

A metalloporphyrin 15, sometimes referred to as M(TPP), of the present invention is depicted in FIG. 2A. FIG. 2A also depicts various metals of the metalloporphyrins 15 of the present invention, and corresponding metal ion charge to radius ratio (i.e., Z/r Ratio) in reciprocal angstroms. The Z/r Ratio should preferably span a wide range in order to target a wide range of metal ligating analytes. These metalloporphyrins have excellent chemical stability on the solid support and most have well-studied solution ligation chemistry. Reverse phase silica was chosen as a non-interacting dispersion medium for the metalloporphyrin array 16 depicted in FIG. 2B, as well as a suitable surface for diffuse reflectance spectral measurements. More importantly, the reverse phase silica presents a hydrophobic interface, which virtually eliminates interference from ambient water vapor. After spotting, sensor plates 18 like the one depicted in FIG. 2B were dried under vacuum at 50° C. for 1 hour prior to use. Thus, immobilization of the metalloporphyrins on a reverse phase silica support is obtained. While ten (10) different metalloporphyrins are shown in FIG. 2A, those of skill in the art will recognize that many other metalloporphyrins are useful in accordance with the present invention. Those of skill in the art will further recognize that in accordance with the broad teachings of the present invention, any dyes capable of changing color upon interacting with an analyte, both containing and not containing metal ions, are useful in the array of the present invention.

Colorimetric Analysis Using the Sensor Plate

For the detection and analysis of odorants in accordance with the present invention, one needs to monitor the absorbance of the sensor plate at one or more wavelengths in a spatially resolved fashion. This can be accomplished with an imaging spectrophotometer, a simple flatbed scanner (e.g. a Hewlett Packard Scanjet 3c), or an inexpensive video or CCD camera.

Figure 3A:
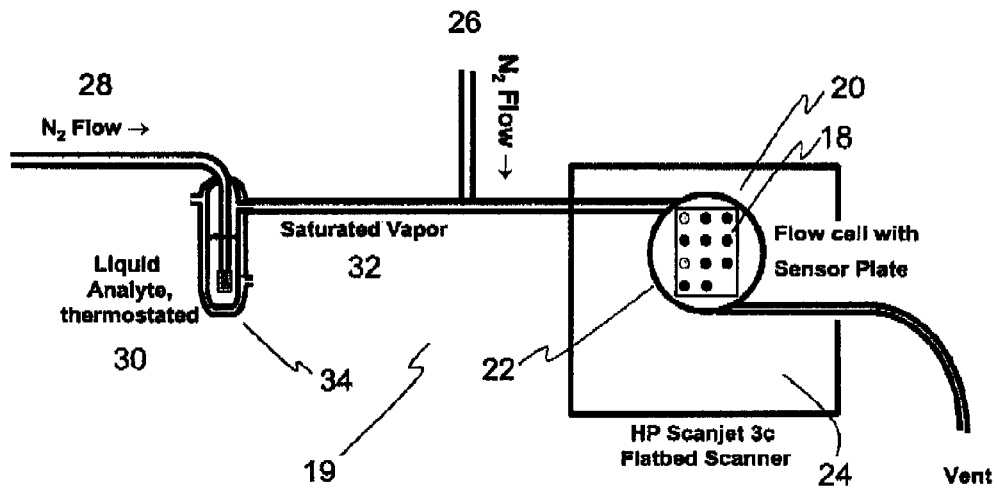
FIG. 3A illustrates a vapor exposure apparatus for demonstration of the present invention.
Figure 3B:
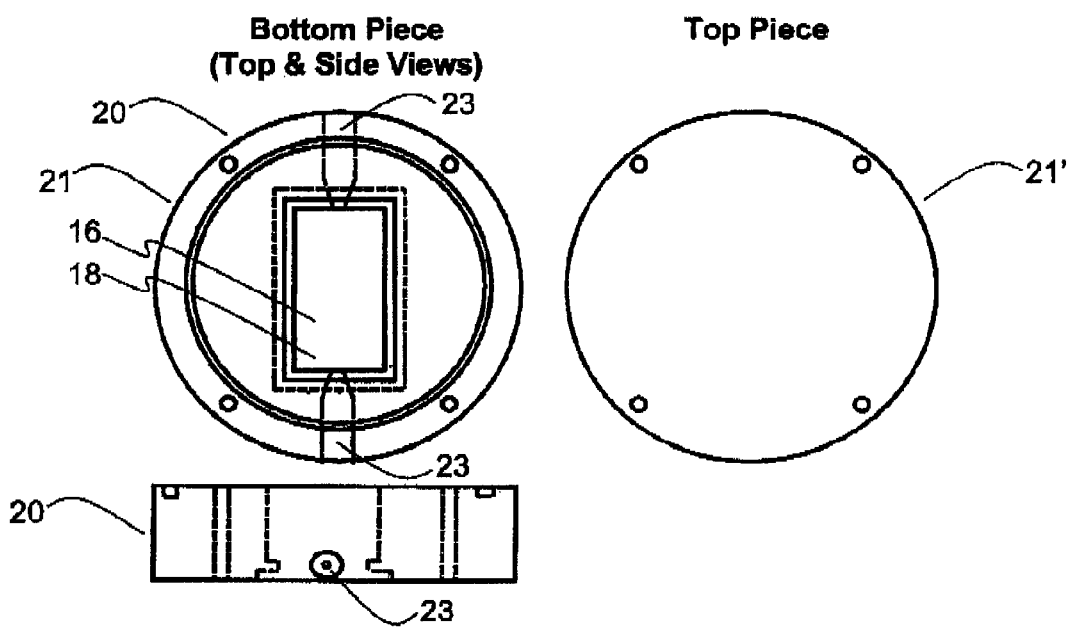
FIG. 3B illustrates a vapor exposure apparatus for demonstration of the present invention.

FIG. 3A illustrates a vapor exposure apparatus 19 of the present invention. FIG. 3B Iillustrates top and side views of bottom piece 21 and a top view of top piece 21' of a vapor exposure flow cell 20 of the present invention. In an embodiment of the present invention for purposes of demonstration, each sensor plate 18 was placed inside of a stainless steel flow cell 20 equipped with a quartz window 22 as shown in FIGS. 3A and 3B. Scanning of the sensor plate 18 was done on a commercially available flatbed scanner 24 (Hewlett Packard Scanjet 3c) at 200 dpi resolution, in fall color mode. Following an initial scan, a control run with a first pure nitrogen flow stream 26 was performed. The array 16 of plate 18 was then exposed to a second nitrogen flow stream 28 saturated with a liquid analyte 30 of interest. As shown in FIG. 3A, the nitrogen flow stream 28 saturated with liquid analyte 30 results in a saturated vapor 32. Saturated vapor 32, containing the analyte 30 of interest were generated by flowing nitrogen flow stream 28 at 0.47 L/min. through the neat liquid analyte 30 in a water-jacketed, glass fritted bubbler 34. Vapor pressures were controlled by regulating the bubbler 34 temperature. As shown in FIG. 3B, vapor channels 23 permit vapor flow to sensor plate 18.

EXAMPLE 1

Scanning at different time intervals and subtracting the red, green and blue ("RGB") values of the new images from those of the original scan yields a color change profile. This is shown for n-butylamine in FIG. 4, in which color change profiles of the metalloporphyrin sensor array 16 as a function of exposure time to n-butylamine vapor. Subtraction of the initial scan from a scan after 5 min. of $N_2$ exposure was used as a control, giving a black response, as shown. 9.3% n-butylamine in $N_2$ was then passed over the array and scans made after exposure for 30 s, 5 min., and 15 min. The red, green and blue ("RGB") mode images were subtracted (absolute value) to produce the color change profiles illustrated. Virtually all porphyrins are saturated after 30 seconds of exposure, yielding a color fingerprint unique for each class of analytes, which is illustrated in FIG. 4.

Figure 4:
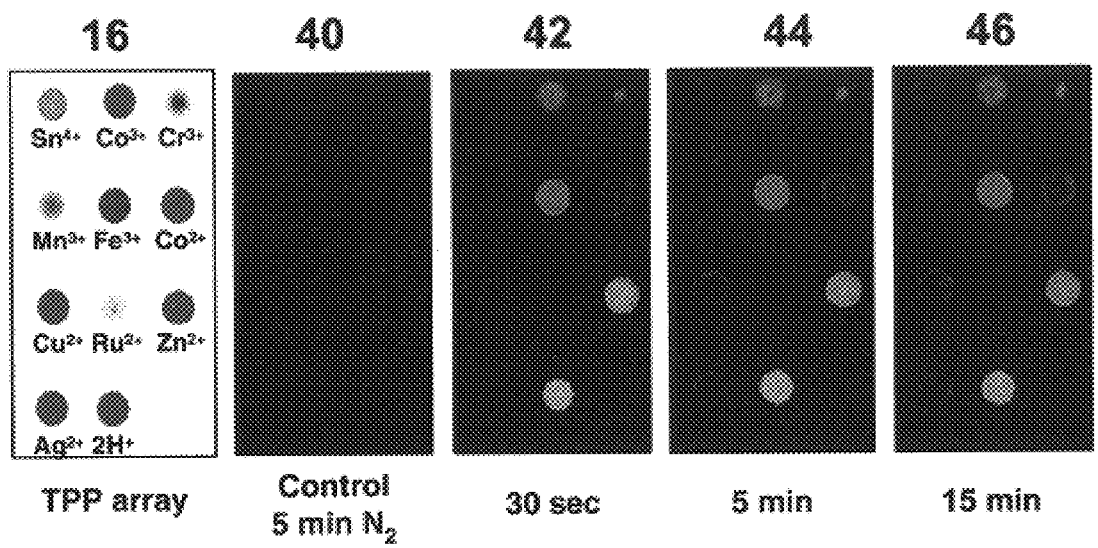
FIG. 4 illustrates the color change profile in a metalloporphyrin array of FIG. 2 when used in the vapor exposure apparatus of FIG. 3A to detect n-butylamine. Metalloporphyrins were immobilized on reverse phase silica gel plates.

More specifically, subtraction of the initial scan 40 from a scan after 5 min. of $N_2$ exposure was used as a control, giving a black response, as shown in FIG. 4. A nitrogen flow stream containing 0.093% n-butylamine was then passed over the array 16 and scans 42, 44, and 46 were made after exposure for 30 seconds, 5 minutes, and 15 minutes, respectively. The RGB mode images were subtracted (absolute value) using Adobe Photoshop™ (which comprises standard image analyzing software), with contrast enhancement by expanding the pixel range (a 32 value range was expanded to 256 each for the R, G, and B values). Subtraction of exposed and unexposed images gives color change patterns that vary in hue and intensity. Because differentiation is provided by an array of detectors, the system has parallels the mammalian olfactory system. As shown in FIG. 4 and summarized in Table 2 below, the dyes have the following colors in scans 42, 44, and 46.

TABLE 2

(Summarizing Colors of Dyes in FIG. 4, Scans 42, 44, and 46)

| | | |
|---|---|---|
| $Sn^{4+}$ -- No Change | $Co^{3+}$ -- Green | $Cr^{3+}$ -- Green |
| $Mn^{3+}$ -- No Change | $Fe^{3+}$ -- Red | $Co^{2+}$ -- Faint Green |
| $Cu^{2+}$ -- No Change | $Ru^{2+}$ -- No Change | $Zn^{2+}$ -- Light Green |
| $Ag^{2+}$ -- No Change | $2H^+$ (Free Base "FB") - Light Blue | |

As summarized in Table 3 below, for the TTP array 16 depicted on the left-hand side of FIG. 4, the dyes have the following colors.

TABLE 3

| | | |
|---|---|---|
| $Sn^{4+}$ -- Greenish Yellow | $Co^{3+}$ -- Red | $C^{3+}$ -- Yellow with Dark Red Center |

TABLE 3-continued

| | | |
|---|---|---|
| $Mn^{3+}$ -- Greenish Yellow | $Fe^{3+}$ -- Dark Red | $Co^{2+}$ -- Red |
| $Cu^{2+}$ -- Red | $Ru^{2+}$ -- Light Yellow | $Zn^{2+}$ -- Red |
| $Ag^{2+}$ -- Red | $2H^+$ (Free Base "FB") - Red | |

EXAMPLE 2

Visible spectral shifts and absorption intensity differences occur upon ligation of the metal center, leading to readily observable color changes. As is well known to those with skill in the art, the magnitude of spectral shift correlates with the polarizability of the ligand; hence, there exists an electronic basis for analyte distinction. Using metal centers that span a range of chemical hardness and ligand binding affinity, a wide range of volatile analytes (including soft ligands, such as thiols, and harder ligands, such as amines) are differentiable. Because porphyrins have been shown to exhibit wavelength and intensity changes in their absorption bands with varying solvent polarity, it is contemplated that the methods and apparatus of the present invention can be used to colorimetrically distinguish among a series of weakly ligating solvent vapors (e.g., arenes, halocarbons, or ketones), as shown for example in FIG. 5.

Figure 5:
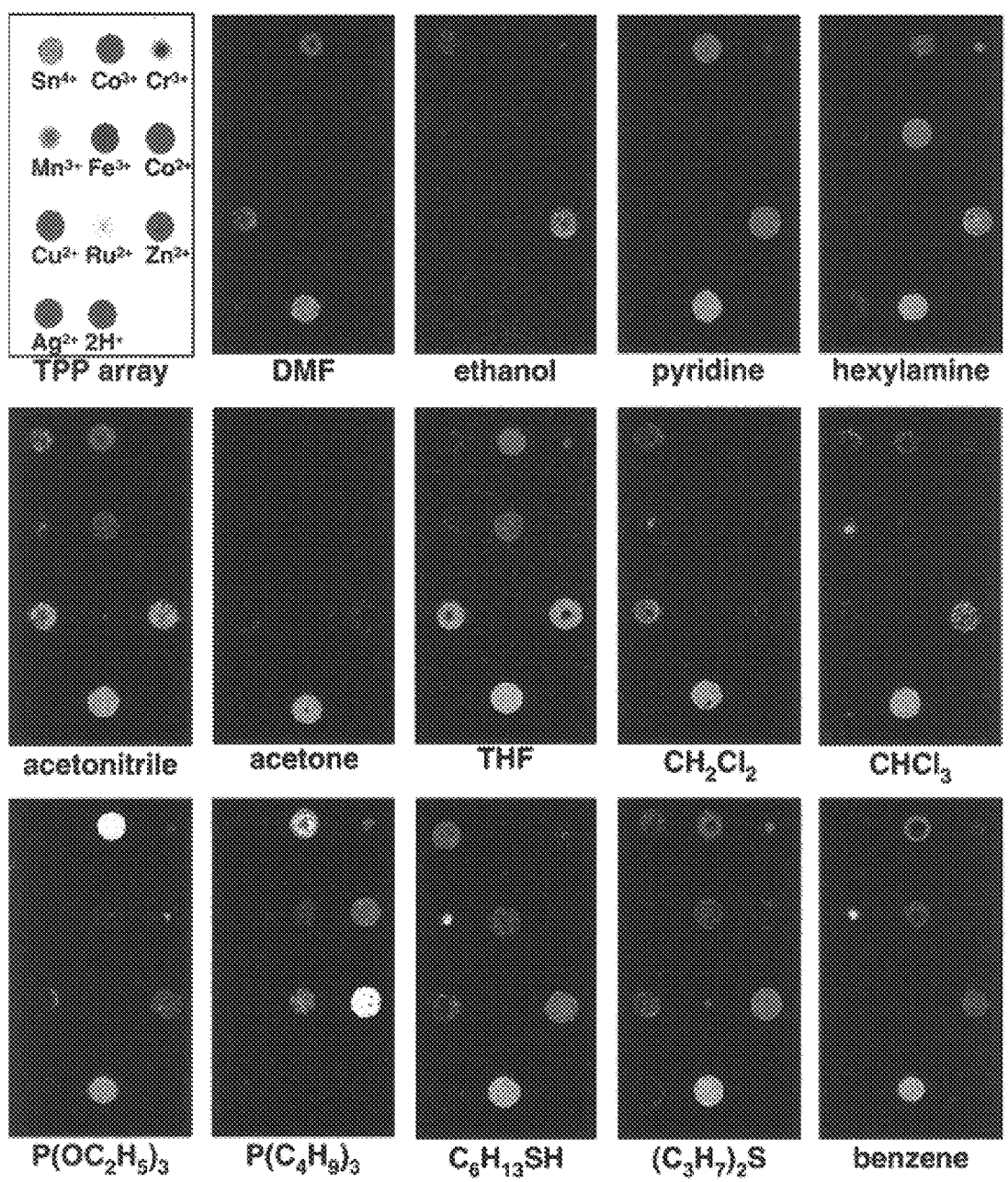
FIG. 5 illustrates a comparison of color changes at saturation for a wide range of analytes. Each analyte was delivered to the array as a nitrogen stream saturated with the analyte vapor at 20° C. DMF stands for dimethylformamide; TBF stands for tetrahydroflran.

A comparison of color changes at saturation for a wide range of analytes is shown in FIG. 5. Each analyte is identified under the colored array 16 that identifies each analyte. ). DMF stands for the analyte dimethylformamide, and THF stands for the analyte tetrahydrofaran. As shown in FIG. 5 and summarized in Table 4 below, the colors of each dye in response to a particular analyte are as follows.

TABLE 4

| Analyte: DMF | | |
|---|---|---|
| $Sn^{4+}$ -- No Change | $Co^{3+}$ -- Green | $Cr^{3+}$ -- No Change |
| $Mn^{3+}$ -- No Change | $Fe^{3+}$ -- No Change | $Co^{2+}$ -- No Change |
| $Cu^{2+}$ -- Blue | $Ru^{2+}$ -- No Change | $Zn^{2+}$ -- No Change |
| $Ag^{2+}$ -- No Change | $2H^+$ (Free Base "FB") - Blue | |
| Analyte: Ethanol | | |
| $Sn^{4+}$ -- Dark Blue | $Co^{3+}$ -- No Change | $Cr^{3+}$ -- Red |
| $Mn^{3+}$ -- No Change | $Fe^{3+}$ -- No Change | $Co^{2+}$ -- No Change |
| $Cu^{2+}$ -- No Change | $Ru^{2+}$ -- No Change | $Zn^{2+}$ -- Blue |
| $Ag^{2+}$ -- No Change | $2H^+$ (Free Base "FB") - No Change | |
| Analyte: Pyridine | | |
| $Sn^{4+}$ -- No Change | $Co^{3+}$ -- Green | $Cr^{3+}$ -- Dark Green |
| $Mn^{3+}$ -- No Change | $Fe^{3+}$ -- No Change | $Co^{2+}$ -- No Change |
| $Cu^{2+}$ -- No Change | $Ru^{2+}$ -- No Change | $Zn^{2+}$ -- Green |
| $Ag^{2+}$ -- No Change | $2H^+$ (Free Base "FB") - Blue | |
| Analyte: Hexylamine | | |
| $Sn^{4+}$ -- No Change | $Co^{3+}$ -- Dark Green | $Cr^{3+}$ -- Green |
| $Mn^{3+}$ -- No Change | $Fe^{3+}$ -- Red | $Co^{2+}$ -- No Change |
| $Cu^{2+}$ -- Blue | $Ru^{2+}$ -- No Change | $Zn^{2+}$ -- Green |
| $Ag^{2+}$ -- Dark Blue | $2H^+$ (Free Base "FB") - Blue | |
| Analyte: Acetonitrile | | |
| $Sn^{4+}$ -- Blue | $Co^{3+}$ -- Dark Green | $Cr^{3+}$ -- No Change |
| $Mn^{3+}$ -- Yellow | $Fe^{3+}$ -- Dark Green | $Co^{2+}$ -- No Change |
| $Cu^{2+}$ -- Blue | $Ru^{2+}$ -- Blue (faint dot) | $Zn^{2+}$ -- Blue |
| $Ag^{2+}$ -- No Change | $2H^+$ (Free Base "FB") - Blue | |
| Analyte: Acetone | | |
| $Sn^{4+}$ -- No Change | $Co^{3+}$ -- No Change | $Cr^{3+}$ -- Red (small dot) |
| $Mn^{3+}$ -- No Change | $Fe^{3+}$ -- No Change | $Co^{2+}$ -- No Change |

TABLE 4-continued

| | | |
|---|---|---|
| $Cu^{2+}$ -- Dark Blue | $Ru^{2+}$ -- No Change | $Zn^{2+}$ -- Dark Blue |
| $Ag^{2+}$ -- No Change | $2H^+$ (Free Base "FB") - Blue | |
| | Analyte: THF | |
| $Sn^{4+}$ -- Dark Blue | $Co^{3+}$ -- Green | $Cr^{3+}$ -- Red |
| $Mn^{3+}$ -- Blue (small dot) | $Fe^{3+}$ -- Dark Green | $Co^{2+}$ -- No Change |
| $Cu^{2+}$ -- Blue | $Ru^{2+}$ -- No Change | $Zn^{2+}$ -- Blue |
| $Ag^{2+}$ -- No Change | $2H^+$ (Free Base "FB") - Blue | |
| | Analyte: $CH_2Cl_2$ | |
| $Sn^{4+}$ -- Dark Blue | $Co^{3+}$ -- No Change | $Cr^{3+}$ -- No Change |
| $Mn^{3+}$ -- Yellow and Red (small dot) | $Fe^{3+}$ -- No Change | $Co^{2+}$ -- No Change |
| $Cu^{2+}$ -- Dark Blue | $Ru^{2+}$ -- No Change | $Zn^{2+}$ -- No Change |
| $Ag^{2+}$ -- No Change | $2H^+$ (Free Base "FB") - Blue | |
| | Analyte: $CHCl_3$ | |
| $Sn^{4+}$ -- Dark Blue | $Co^{3+}$ -- Dark Green | $Cr^{3+}$ -- Yellow (circle) |
| $Mn^{3+}$ -- Yellow | $Fe^{3+}$ -- Dark Green (very faint) | $Co^{2+}$ -- No Change |
| $Cu^{2+}$ -- Dark Blue (very faint) | $Ru^{2+}$ -- No Change | $Zn^{2+}$ -- Blue |
| $Ag^{2+}$ -- Blue (very faint) | $2H^+$ (Free Base "FB") - Blue | |
| | Analyte: $P(OC_2H_5)_3$ | |
| $Sn^{4+}$ -- No Change | $Co^{3+}$ -- Yellow | $Cr^{3+}$ -- Dark Green |
| $Mn^{3+}$ -- No Change | $Fe^{3+}$ -- Dark Green (very faint) | $Co^{2+}$ -- Greenish Yellow |
| $Cu^{2+}$ -- Dark Blue (faint) | $Ru^{2+}$ -- No Change | $Zn^{2+}$ -- Greenish Blue |
| $Ag^{2+}$ -- Blue (very faint) | $2H^+$ (Free Base "FB") - Blue | |
| | Analyte: $P(C_4H_9)_3$ | |
| $Sn^{4+}$ -- No Change | $Co^{3+}$ -- Yellow and Red | $Cr^{3+}$ -- Deep Red |
| $Mn^{3+}$ -- No Change | $Fe^{3+}$ -- Dark Green (faint) | $Co^{2+}$ -- Red (with some yellow) |
| $Cu^{2+}$ -- No Change | $Ru^{2+}$ -- Dark Blue | $Zn^{2+}$ -- Yellow |
| $Ag^{2+}$ -- No Change | $2H^+$ (Free Base "FB") - No Change | |
| | Analyte: $C_6H_{13}SH$ | |
| $Sn^{4+}$ -- Green | $Co^{3+}$ -- No Change | $Cr^{3+}$ -- Yellow circle surrounded by greenish blue circle |
| $Mn^{3+}$ -- Yellow | $Fe^{3+}$ -- Dark Green | $Co^{2+}$ -- No Change |
| $Cu^{2+}$ -- Dark Blue (faint) | $Ru^{2+}$ -- No Change | $Zn^{2+}$ -- Green |
| $Ag^{2+}$ -- Blue (very faint) | $2H^+$ (Free Base "FB") - Blue | |
| | Analyte: $(C_3H_7)_2S$ | |
| $Sn^{4+}$ -- Dark Blue (faint) | $Co^{3+}$ -- Deep Green | $Cr^{3+}$ -- Green |
| $Mn^{3+}$ -- No Change | $Fe^{3+}$ -- Dark Green | $Co^{2+}$ -- Dark Green (very faint) |
| $Cu^{2+}$ -- Dark Blue (faint) | $Ru^{2+}$ -- Green | $Zn^{2+}$ -- Green |
| $Ag^{2+}$ -- Blue (very faint) | $2H^+$ (Free Base "FB") - Blue | |
| | Analyte: Benzene | |
| $Sn^{4+}$ -- No Change | $Co^{3+}$ -- Green | $Cr^{3+}$ -- Yellow (very faint) |
| $Mn^{3+}$ -- Yellow (some green) | $Fe^{3+}$ -- Dark Green | $Co^{2+}$ -- No Change |
| $Cu^{2+}$ -- No Change | $Ru^{2+}$ -- No Change | $Zn^{2+}$ -- Dark Green |
| $Ag^{2+}$ -- No Change | $2H^+$ (Free Base "FB") - Blue | |

The degree of ligand softness (roughly their polarizability) increases from left to right, top to bottom as shown in FIG. 1. Each analyte is easily distinguished from the others, and there are family resemblances among chemically similar species (e.g., pyridine and n-hexylamine). Analyte distinction originates both in the metal-specific ligation affinities and in their specific, unique color changes upon ligation. Each analyte was delivered to the array as a nitrogen stream saturated with the analyte vapor at 20° C. (to ensure complete saturation, 30 min. exposures to vapor were used. Although these fingerprints were obtained by exposure to saturated vapors (thousands of ppm), unique patterns can be identified at much lower concentrations.

The metalloporphyrin array 16 has been used to quantify single analytes and to identify vapor mixtures. Because the images' color channel data (i.e., RGB values) vary linearly with porphyrin concentration, we were able to quantify single porphyrin responses to different analytes. Color channel data were collected for individual spots and plotted, for example, as the quantity $(R_{plt}-R_{spt})/(R_{plt})$, where $R_{plt}$ was the red channel value for the initial silica surface and $R_{spt}$ the average value for the spot. For example, Fe(TFPP)(Cl) responded linearly to octylamine between 0 and 1.5 ppm. Other porphyrins showed linear response ranges that varied with ligand affinity (i.e., equilibrium constant).

EXAMPLE 3

Figure 6:
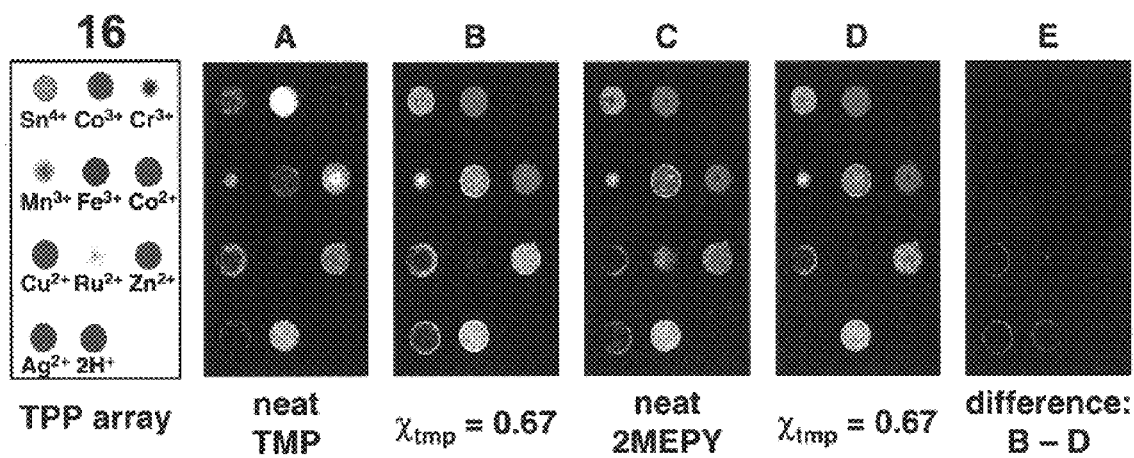
FIG. 6 illustrates two component saturation responses of mixtures of 2-methylpyridine and trimethylphosphite. Vapor mixtures were obtained by mixing two analyte-saturated $N_2$ streams at variable flow ratios.

The array of the present invention has demonstrated interpretable and reversible responses even to analyte mixtures of strong ligands, such as pyridines and phosphites, as is shown in FIG. 6. Color change patterns for the mixtures are distinct from either of the neat vapors. Good reversibility was demonstrated for this analyte pair as the vapor mixtures were cycled between the neat analyte extremes, as shown in FIG. 6, which shows the two component saturation responses to mixtures of 2-methylpyridine ("2MEPY") and trimethylphosphite ("TMP"). Vapor mixtures were obtained by mixing the analyte-saturated $N_2$ streams at variable flow ratios. A single plate was first exposed to pure trimethylphosphite vapor in $N_2$ (Scan A), followed by increasing mole fractions of 2-methylpyridine up to pure 2-methylpyridine vapor (Scan C), followed by decreasing mole fractions of 2-methylpyridine back to pure trimethylphosphite vapor. In both directions, scans were taken at the same mole fraction trimethylphosphite and showed excellent reversibility; scans at mole fractions at 67% trimethylphosphite ($\chi_{tmp}$=0.67, Scans B and D) and of their difference map are shown (Scan E). Response curves for the individual porphyrins allow for quantification of the mixture composition. The colors of each dye upon exposure to the analytes TMP and 2MEPY are shown in FIG. 6 and are summarized in Table 5 below.

TABLE 5

| | Scan A, Analyte: Neat TMP | |
|---|---|---|
| $Sn^{4+}$ -- Dark Blue | $Co^{3+}$ -- Yellow | $Cr^{3+}$ -- No Change |
| $Mn^{3+}$ -- Yellow with red center | $Fe^{3+}$ -- Dark Green | $Co^{2+}$ -- Greenish Yellow |
| $Cu^{2+}$ -- Dark Blue | $Ru^{2+}$ -- No Change | $Zn^{2+}$ -- Blue |
| $Ag^{2+}$ -- Green (very faint) | $2H^+$ (Free Base "FB") - Reddish Blue | |
| | Scan B, Analyte: TMP,$x_{TMP}$ = 0.67 | |
| $Sn^{4+}$ -- Blue | $Co^{3+}$ -- Green | $Cr^{3+}$ -- Green (small dot) |
| $Mn^{3+}$ -- Yellow and Green | $Fe^{3+}$ -- Green and Yellow | $Co^{2+}$ -- Green with red center |
| $Cu^{2+}$ -- Dark Blue | $Ru^{2+}$ -- Purple (very faint) | $Zn^{2+}$ -- Blue |
| $Ag^{2+}$ -- Greenish Blue | $2H^+$ (Free Base "FB") - Reddish Blue | |
| | Scan C, Analyte: Neat 2MEPY | |
| $Sn^{4+}$ -- Blue | $Co^{3+}$ -- Green | $Cr^{3+}$ -- No Change |
| $Mn^{3+}$ -- Yellow and Green with Red | $Fe^{3+}$ -- Red with some Yellow | $Co^{2+}$ -- Green |

TABLE 5-continued

| | | |
|---|---|---|
| center | | |
| $Cu^{2+}$ -- Dark Blue | $Ru^{2+}$ -- Deep Blue | $Zn^{2+}$ -- Green with some Blue |
| $Ag^{2+}$ -- Green with some Blue | $2H^+$ (Free Base "FB") - Reddish Blue | |
| | Scan D, Analyte: TMP,$x_{TMP}$ = 0.67 | |
| $Sn^{4+}$ -- Blue | $Co^{3+}$ -- Green | $Cr^{3+}$ -- No Change |
| $Mn^{3+}$ -- Yellow and Green | $Fe^{3+}$ -- Green and Yellow | $Co^{2+}$ -- Green |
| $Cu^{2+}$ -- Dark Blue | $Ru^{2+}$ -- Purple (very faint) | $Zn^{2+}$ -- Blue |
| $Ag^{2+}$ -- Greenish Blue (very faint) | $2H^+$ (Free Base "FB") - Reddish Blue | |
| | Scan E | |
| $Sn^{4+}$ -- No Change | $Co^{3+}$ -- No Change | $Cr^{3+}$ -- No Change |
| $Mn^{3+}$ -- No Change | $Fe^{3+}$ -- No Change | $Co^{2+}$ -- No Change |
| $Cu^{2+}$ -- Blue (very faint) | $Ru^{2+}$ -- Blue (small dot) | $Zn^{2+}$ -- No Change |
| $Ag^{2+}$ -- Blue (very faint) | $2H^+$ (Free Base "FB") - Green | |

EXAMPLE 4

Figure 7:
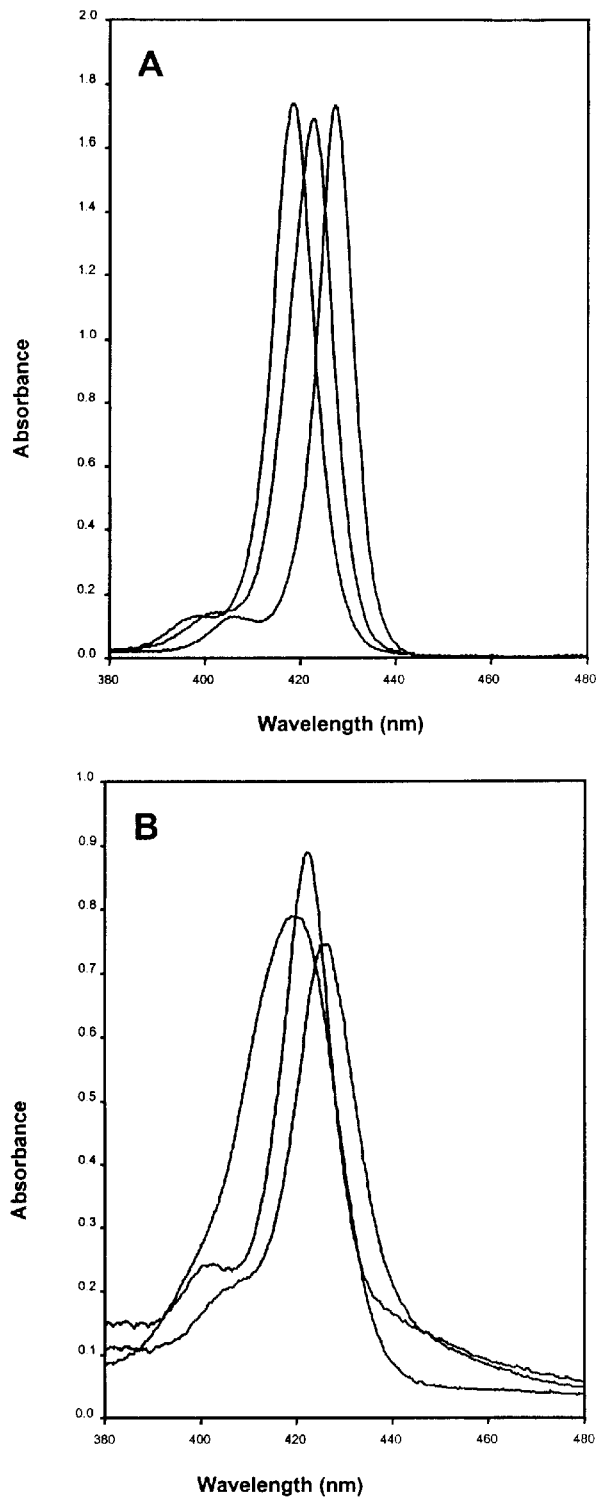
FIG. 7 illustrates a comparison of Zn(TPP) spectral shifts upon exposure to ethanol and pyridine (py) in methylene chloride solution (A) and on the reverse phase support (B).

In an effort to understand the origin of the color changes upon vapor exposure, diffuse reflectance spectra were obtained for single porphyrin spots before and after exposure to analyte vapors. Porphyrin solutions were spotted in 50 μL aliquots onto a plate and allowed to dry under vacuum at 50° C. Diffuse reflectance spectra of the plate were then taken using a UV-visible spectrophotometer equipped with an integrating sphere. Unique spectral shifts were observed upon analyte exposure, which correlated well with those seen from solution ligation. For example, Zn(TPP) exposure to ethanol and pyridine gave unique shifts which were very similar to those resulting from ligand exposure in solution. FIG. 7 shows a comparison of Zn(TPP) spectral shifts upon exposure to ethanol and pyridine (py) in methylene chloride solution (A) and on the reverse phase support (B). In both A and B, the bands correspond, from left to right, to Zn(TPP), Zn(TPP)(C$_2$H$_5$OH), and Zn(TPP)(py), respectively. Solution spectra (A) were collected using a Hitachi U-3300 spectrophotometer; Zn(TPP), C$_2$H$_5$OH, and py concentrations were approximately 2 μM, 170 mM, and 200 μM, respectively. Diffuse reflectance spectra (B) were obtained with an integrating sphere attachment before exposure to analytes, after exposure to ethanol vapor in N$_2$, and after exposure to pyridine vapor in N$_2$ for 30 min. each using the flow cell.

Improvement to Low Concentration Response

Color changes at levels as low as 460 ppb have been observed for octylamine vapor, albeit with slow response times due to the high surface area of the silica on the plate 18. The surface area of C2 plates is ≈350 m$^2$/gram. Removal of excess silica gel surrounding the porphyrin spots from the plate 18 led to substantial improvements in response time for exposures to trace levels of octylamine. Because the high surface area of the reverse phase silica surface is primarily responsible for the increased response time, other means of solid support or film formation can be used to improve low concentration response.

Further, the present invention contemplates miniaturization of the array using small wells 60 (<1 mm), for example in glass, quartz, or polymers, to hold metalloporphyrin or other dyes as thin films, which are deposited as a solution, by liquid droplet dispersion (e.g., airbrush or inkjet), or deposited as a solution of polymer with metalloporphyrin.

Figure 8:
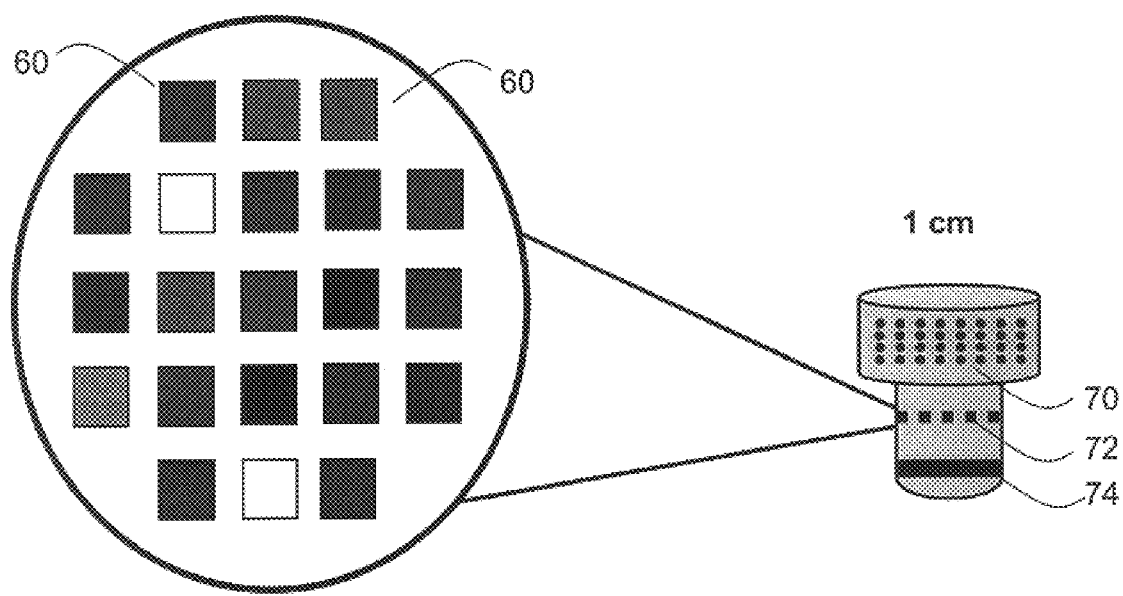
FIG. 8 illustrates another embodiment of the present invention, and more particularly, an small array comprising microwells built into a wearable detector which also contains a portable light source and a light detector, such as a charge-coupled device (CCD) or photodiode array.
Figure 9:
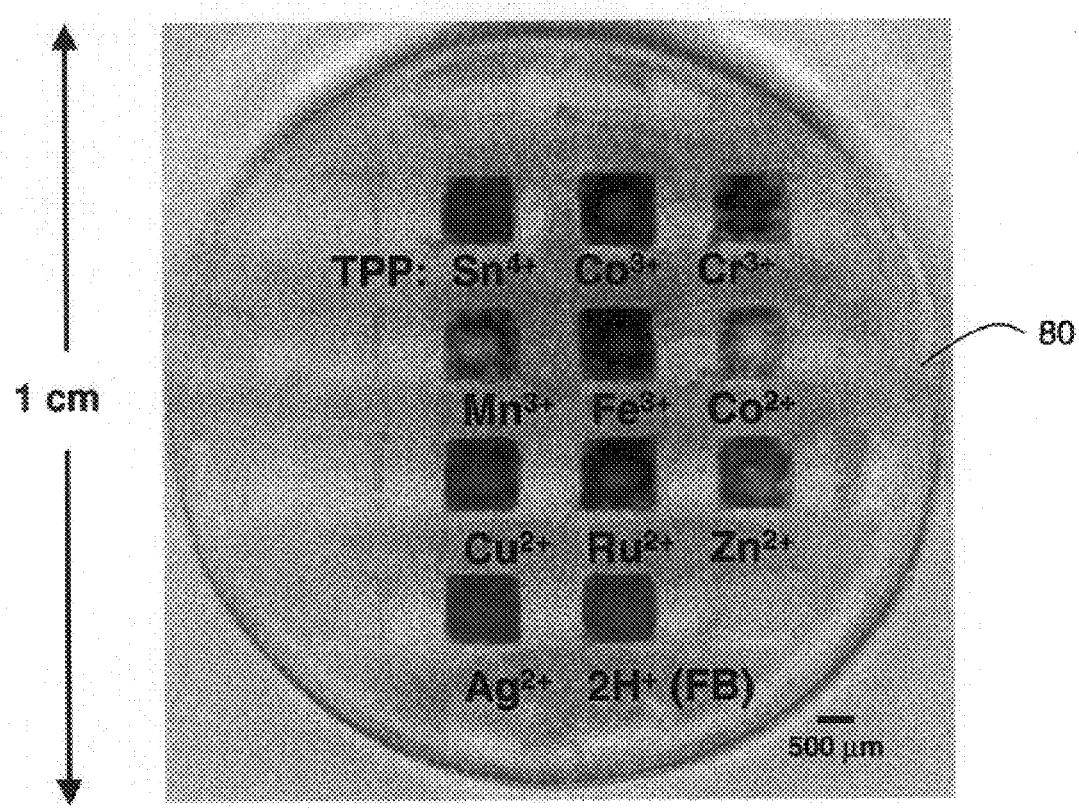
FIG. 9 illustrates another embodiment of the present invention, and more particularly, a microwell porphyrin array wellplate constructed from polydimethylsiloxane (PDMS).
Figure 10:
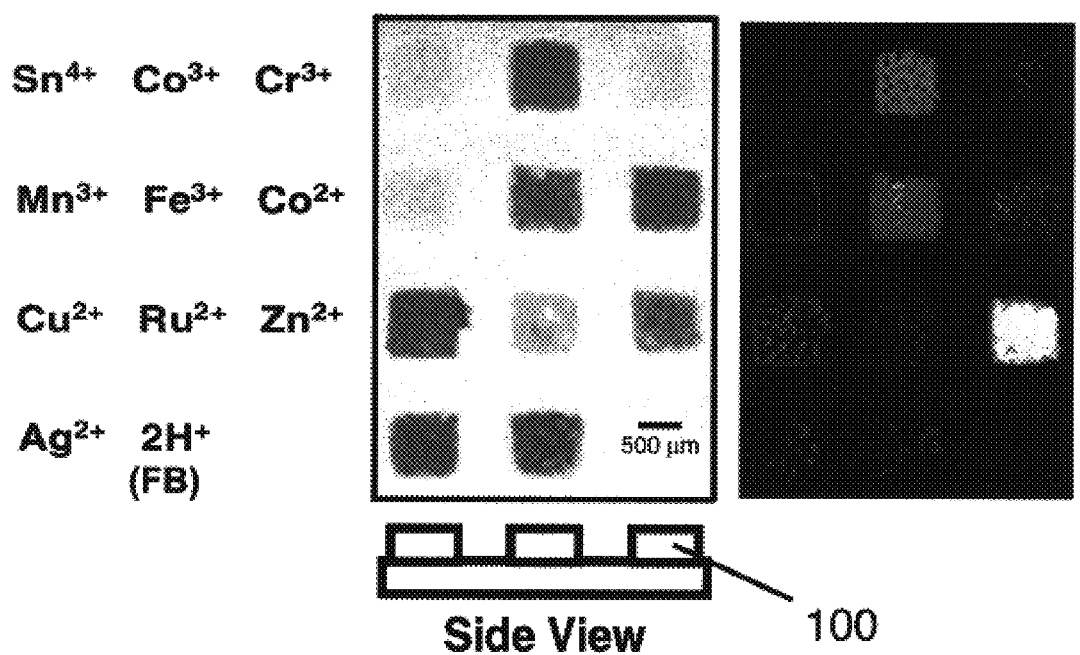
FIG. 10 illustrates another embodiment of the present invention, and more particularly, a microplate containing machined teflon posts, upon which the porphyrin array is immobilized in a polymer matrix (polystyrene/dibutylphthalate).

These embodiments are depicted in FIGS. 8, 9, and 10. FIG. 8 illustrates the interfacing of a microplate 60 into an assembly consisting of a CCD 70, a microplate 72 and a light source 74. FIG. 9 illustrates another embodiment of the present invention, and more particularly, a microwell porphyrin array wellplate 80 constructed from polydimethylsiloxane (PDMS). The colors of the dyes shown in FIG. 9 are summarized below in Table 6.

TABLE 6

| | | |
|---|---|---|
| $Sn^{4+}$ -- Dark Red | $Co^{3+}$ -- Dark Red | $Cr^{3+}$ -- Dark Green |
| $Mn^{3+}$ -- Green | $Fe^{3+}$ -- Dark Red | $Co^{2+}$ -- Yellowish Green |
| $Cu^{2+}$ -- Deep Red | $Ru^{2+}$ -- Dark Red | $Zn^{2+}$ -- Red with some Yellow |
| $Ag^{2+}$ -- Red | $2H^+$ (Free Base "FB") - Red | |

FIG. 10 demonstrates deposition of metalloporphyrin/polymer (polystyrene/dibutylphthalate) solutions upon a plate, which includes a series of micro-machined Teflon® posts 100 having the same basic position relative to each other as shown in FIG. 2A and FIG. 2B. The colors for the dyes in the middle of FIG. 10 are summarized in Table 7 below.

TABLE 7

| | | |
|---|---|---|
| $Sn^{4+}$ -- Yellow | $Co^{3+}$ -- Orange | $Cr^{3+}$ -- Yellow |
| $Mn^{3+}$ -- Yellow | $Fe^{3+}$ -- Orange | $Co^{2+}$ -- Orange |
| $Cu^{2+}$ -- Orange | $Ru^{2+}$ -- Dark Yellow | $Zn^{2+}$ -- Orange |
| $Ag^{2+}$ -- Orange | $2H^+$ (Free Base "FB") - Red | |

The colors for the dyes on the right hand side of FIG. 10 are summarized in Table 8 below.

TABLE 8

| | | |
|---|---|---|
| $Sn^{4+}$ -- No Change | $Co^{3+}$ -- Green | $Cr^{3+}$ -- Red |
| $Mn^{3+}$ -- Blue | $Fe^{3+}$ -- Red | $Co^{2+}$ -- Red, Green, Blue, and Yellow |
| $Cu^{2+}$ -- Green with some Blue | $Ru^{2+}$ -- Blue (very faint) | $Zn^{2+}$ -- Yellow with some Red |
| $Ag^{2+}$ -- Green with some Blue | $2H^+$ (Free Base "FB") - Green with some Blue | |

EXAMPLE 5

Figure 11:
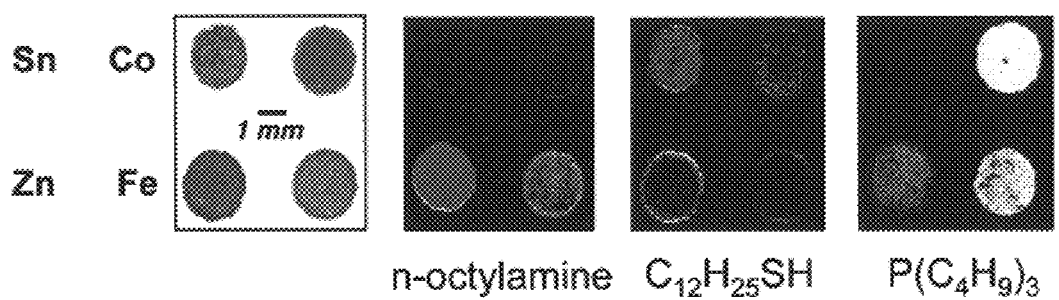
FIG. 11 illustrates another embodiment of the present invention, showing a microplate of the type shown in FIG. 10, consisting of a minimized array of four metalloporphyrins, showing the color profile changes for n-octylamine, dodecanethiol, and tri-n-butylphosphine, each at 1.8 ppm.

FIG. 11 shows the color profile changes from a microplate of the type shown in FIG. 10. The microplate, consisting of a mninimized array of four metalloporphyrins, i.e., Sn(TPP)(Cl$_2$), Co(TPP)(Cl), Zn(TPP), Fe(TFPP)(Cl), clockwise from the upper left (where TFPP stands for 5,10,15,20-tetrakis(pentafluorophenyl)porphyrinate). The color profile changes are shown in FIG. 11 after exposure to low levels of n-octylamine, dodecanethiol (C$_{12}$H$_{25}$ SH), and tri-n-butylphosphine (P(C$_4$H$_9$)$_3$), each at 1.8 ppm, which is summarized in Table 9 below.

TABLE 9

| Dyes on Teflon ® | |
|---|---|
| Sn - Dark Yellow | Co - Red |
| Zn - Red | Fe - Orange with Red outline |
| Dyes exposed to n-octylamine | |
| Sn - No Change | Co - Green (very faint) |
| Zn - Red | Fe - Green |
| Dyes exposed to C$_{12}$H$_{25}$SH | |
| Sn - Red | Co - Green with some red, yellow and blue (faint) |

TABLE 9-continued

| | |
|---|---|
| Zn - Red with some green and yellow | Fe - Blue (very faint) |
| Dyes exposed to P(C$_4$H$_9$)$_3$ | |
| Sn - No Change | Co - Yellow with red center and some red periphery |
| Zn - Green | Fe - Yellow with some Green and Blue |

The low ppm levels of octylamine, an analyte of interest, were generated from temperature-regulated octylaminel-dodecane solutions with the assumption of solution ideality. The dodecane acts as a diluent to lower the level of octylamine vapor pressure for the purposes of this demonstration of the invention.

EXAMPLE 6

Figure 12:
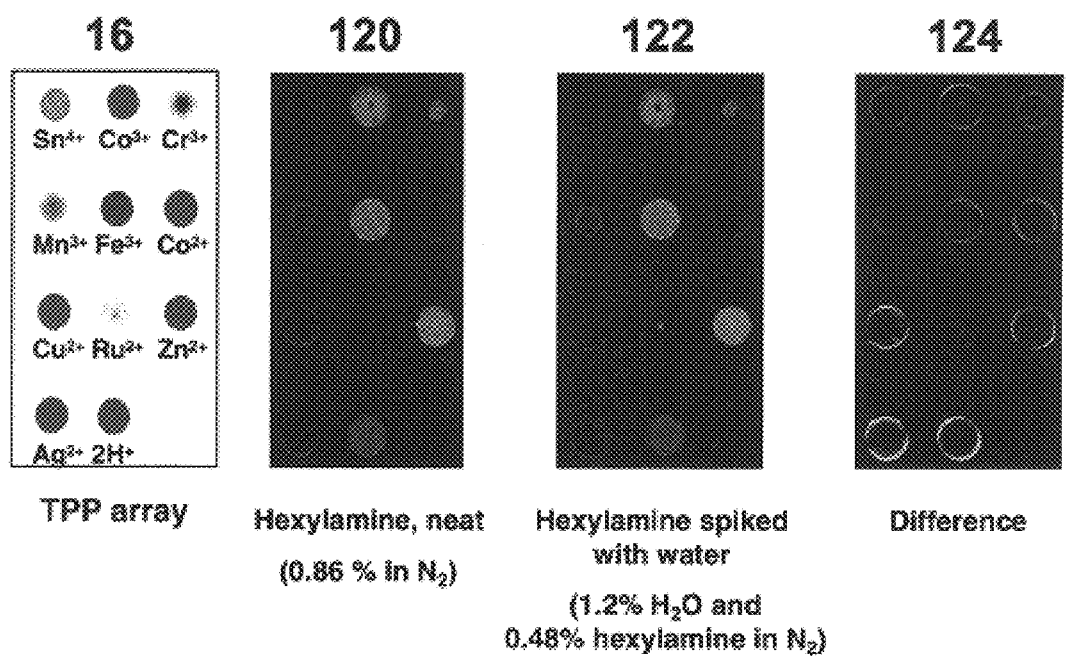
FIG. 12 illustrates the immunity of the present invention to interference from water vapor.

FIG. 12 illustrates the immunity of the present invention to interference from water vapor. The hydrophobicity of the reverse phase support greatly any possible effects from varying water vapor in the atmosphere to be tested. For instance, as shown in FIG. 12, a color fingerprint generated from exposure of the array to n-hexylamine (0.86% in N$_2$) was identical to that for n-hexylamine spiked heavily with water vapor (1.2% H$_2$O, 0.48% hexylamine in N$_2$). See scans 120, 122 and 124. The ability to easily detect species in the presence of a large water background represents a substantial advantage over mass-sensitive sensing techniques or methodologies that employ polar polymers as part of the sensor array. The color patterns shown in FIG. 12 are summarized in Table 10 below.

TABLE 10

Scan 120

| | | |
|---|---|---|
| Sn$^{4+}$ -- No Change | Co$^{3+}$ -- Green | Cr$^{3+}$ -- Green |
| Mn$^{3+}$ -- No Change | Fe$^{3+}$ -- Red | Co$^{2+}$ -- No Change |
| Cu$^{2+}$ -- No Change | Ru$^{2+}$ -- No Change | Zn$^{2+}$ -- Green |
| Ag$^{2+}$ -- No Change | 2H$^+$ (Free Base "FB") - Dark Blue | |

Scan 122

| | | |
|---|---|---|
| Sn$^{4+}$ -- No Change | Co$^{3+}$ -- Green | Cr$^{3+}$ -- Green |
| Mn$^{3+}$ -- No Change | Fe$^{3+}$ -- Red | Co$^{2+}$ -- No Change |
| Cu$^{2+}$ -- No Change | Ru$^{2+}$ -- Green (small dot) | Zn$^{2+}$ -- Green |
| Ag$^{2+}$ -- No Change | 2H$^+$ (Free Base "FB") - Dark Blue | |

Scan 124

| | | |
|---|---|---|
| Sn$^{4+}$ -- Bluish Circle | Co$^{3+}$ -- Bluish Circle | Cr$^{3+}$ -- Bluish Circle |
| Mn$^{3+}$ -- Bluish Circle | Fe$^{3+}$ -- Bluish Circle | Co$^{2+}$ -- Bluish Circle |
| Cu$^{2+}$ -- Bluish Circle | Ru$^{2+}$ -- Blrnsh Circle | Zn$^{2+}$ -- Bluish Cirde |
| Ag$^{2+}$ -- Bluish Circle | 2H$^+$ (Free Base "FB") - Bluish Circle | |

Additional Features of the Preferred Embodiments of the Invention

Having demonstrated electronic differentiation, an important further goal is the shape-selective distinction of analytes (e.g., n-hexylamine vs. cyclohexylamine). Functionalized metalloporphyrins that limit steric access to the metal ion are candidates for such differentiation. For instance, we have been able to control ligation of various nitrogenous ligands to dendrimer-metalloporphyrins and induce selectivities over a range of more than 10$^4$. As an initial attempt toward shape-selective detection, we employed the slightly-hindered tetrakis(2,4,6-trimethoxyphenyl)porphyrins (TTMPP) in our sensing array. With these porphyrins, fingerprints for t-butylamine and n-butylamine showed subtle distinctions, as did those for cyclohexylamine and n-hexylamine. Using more hindered metalloporphyrins, it is contemplated that the present invention can provide greater visual differentiation. Such porphyrins include those whose periphery is decorated with dendrimer, siloxyl, phenyl, t-butyl and other bulky substituents, providing sterically constrained pockets on at least one face (and preferably both) of the porphyrin.

In a similar fashion, it is contemplated that the sensor plates of the present invention can be used for the detection of analytes in liquids or solutions, or solids. A device that detects an analyte in a liquid or solution or solid can be referred to as an artificial tongue. Proper choice of the metal complexes and the solid support must preclude their dissolution into the solution to be analyzed. It is preferred that the surface support repel any carrier solvent to promote the detection of trace analytes in solution; for example, for analysis of aqueous solutions, reverse phase silica has advantages as a support since it will not be wetted directly by water.

Alternative sensors in accordance with the present invention may include any other dyes or metal complexes with intense absorbance in the ultraviolet, visible, or near infrared spectra that show a color change upon exposure to analytes. These alternative sensors include, but are not limited to, a variety of macrocycles and non-macrocycles such as chlorins and chlorophylls, phthalocyanines and metallophthalocyanines, salen-type compounds and their metal complexes, or other metal-containing dyes.

The present invention can be used to detect a wide variety of analytes regardless of physical form of the analytes. That is, the present invention can be used to detect any vapor emitting substance, including liquid, solid, or gaseous forms, and even when mixed with other vapor emitting substances, such solution mixtures of substances.

The present invention can be used in combinatorial libraries of metalloporphyrins for shape selective detection of substrates where the substituents on the periphery of the macrocycle or the metal bound by the porphyrin are created and then physically dispersed in two dimensions by (partial) chromatographic or electrophoretic separation.

The present invention can be used with chiral substituents on the periphery of the macrocycle for identification of chiral substrates, including but not limited to drugs, natural products, blood or bodily fluid components.

The present invention can be used for analysis of biological entities based on the surface proteins, oligosacharides, antigens, etc., that interact with the metalloporphyrin array sensors of the present invention. Further, the sensors of the present invention can be used for specific recognition of individual species of bacteria or viruses.

The present invention can be used for analysis of nucleic acid sequences based on sequence specific the surface interactions with the metalloporphyrin array sensors. The sensors of the present invention can be used for specific recognition of individual sequences of nucleic acids. Substituents on the porphyrins that would be particularly useful in this regard are known DNA intercalating molecules and nucleic acid oligomers.

The present invention can be used with ordinary flat bed scanners, as well as portable miniaturized detectors, such as CCD detectors with microarrays of dyes such as metalloporphyrins.

The present invention can be used for improved sensitivity, automation of pattern recognition of liquids and solutions, and analysis of biological and biochemical samples.

Many modifications and variations may be made in the techniques and structures described and illustrated herein without departing from the spirit and scope of the present invention. Accordingly, the techniques and structures described and illustrated herein should be understood to be illustrative only and not limiting upon the scope of the present invention.

What is claimed is:

1. An artificial nose comprising an array, the array comprising at least a first dye and a second dye deposited directly onto a single support in a predeternmied pattern combination, the combination of the dyes in the array having a distinct and direct spectral absorbance or reflectance response to disinct analytes, wherein the first dye and the second dye are selected from the group consisting of porphyrin, chlorine chlorophyll, phtahalocyanine, and salen and their metal complexes.

2. The artificial nose of claim 1 wherein the first dye and the second dye are porphyrins.

3. The artificial nose of claim 1 wherein the first dye and the second dye are metalloporphyrins.

4. The artificial nose of claim 3, wherein the first and second metalloporphyrins are from the group of metalloporphyrins depicted in FIG. 2A.

5. The artificial nose of claim 3 wherein the first dye and the second dye are metalloporphyrins having a metal ion selected from the group consisting of $Sn^{4+}$, $Co^{3+}$, $Cr^{3+}$, $Mn^{3+}$, $Fe^{3+}$, $Co^{2+}$, $Cu^{2+}$, $Ru^{2+}$, $Zn^{2+}$, and $Ag^{2+}$.

6. The artificial nose of claim 1 wherein the array is part of a sensor plate.

7. The artificial nose of claim 1 wherein the array is connected to a visual display device.

8. The artificial nose of claim 7 wherein the visual display device comprises a scanner.

9. The artificial nose of claim 7 wherein the visual display device comprises a charge-coupled device.

10. The artificial nose of claim 1 wherein the array is a spatially resolved collection of dyes.

11. The artificial nose of claim 10 wherein the spatially resolved collection of dyes is a spatially resolved combinatorial family of dyes.

12. A method for detecting an analyte comprising the steps of:

forming an array of at least a first dye and a second dye deposited directly onto a single support in a predetemined pattern combination, the combination of dyes in the array having a distinct and direct spectral absorbance or reflectance response to distinct analytes, wherein the first dye and the second dye are selected from the group consisting of porphyrin, chlorin, chlorophyll, phtahalocyanine, and salen and their metal oomplexes, subjecting the way to an analyte, inspecting the array for a distinct and direct spectral absorbance or reflectance response and correlating the distinct and direct spectral response to the presence of the analyte.

13. The method of claim 12 wherein the first dye and second dye are porphyrins.

14. The method of claim 12 wherein the first dye and the second dye are from the group comprising porphyrin, chlorin, chlorophyll, phthalocyanine, or salen.

15. The method of claim 12 wherein the first dye and the second dye are metalloporphyrins.

16. The method of claim 15 wherein the first and second metalloporphyrins dyes are from the group of metalloporphyrins depicted in FIG. 2A.

17. The method of claim 15 wherein the first dye and the second dye are metalloporphyiins having a metal ion selected from the group consisting of $Sn^{4+}$, $Co^{3+}$, $Cr^{3+}$, $Mn^{3+}$, $Fe^{3+}$, $Co^{2+}$, $Cu^{2+}$, $Ru^{2+}$, $Zn^{2+}$, and $Ag^{2+}$.

18. The method of claim 12 having the step of placing the array on a sensor plate.

19. The method of claim 12 having the step of connecting the array to a visual display or detection device.

20. The method of claim 19 wherein the visual display device comprises a scanner.

21. The method of claim 19 wherein the visual display device comprises a charge-coupled device.

22. The method of claim 12 wherein the array is a spatially resolved collection of dyes.

23. The method of claim 22 wherein the spatially resolved collection of dyes is a spatially resolved combinatorial family of dyes.

24. The method of claim 12 having the further step of comparing the spectral response with a catalog of analyte spectral responses to identify the analyte.

25. A artificial tongue comprising an array, the array comprising at least a first dye and a second dye deposited directly onto a single support in a predetermied pattern combination, the combination of dyes in the array having a distinct and direct spectral absorbance or reflectance response to distinct analytes in solution or liquid analytes, or analytes in a solid or solid analytes, wherein the fist dye and the second dye are selected from the group consisting of porphyrin, chlorin, chlorophyll, phtahalocyanine, and salen and their metal complexes.

26. The artificial tongue of claim 25 wherein the first dye and the second dye are porphyrins.

27. The artificial tongue of claim 25 wherein the first dye and the second dye are metalloporphyrins.

28. The artificial tongue of claim 27 wherein the first and second metalloporphyrins are from the group of metalloporphyrins depicted in FIG. 2A.

29. The artificial tongue of claim 27 wherein the first dye and the second dyes are metalloporphyrins having a metal ion selected from the group consisting of $Sn^{4+}$, $Co^{3+}$, $Cr^{3+}$, $Mn^{3+}$, $Fe^{3+}$, $Co^{2+}$, $Cu^{2+}$, $Ru^{2+}$, $Zn^{2+}$, and $Ag^{2+}$.

30. The artificial tongue of claim 25 wherein the array is part of a sensor plate.

31. The artificial tongue of claim 25 wherein the array is connected to a visual display device.

32. The artificial tongue of claim 31 wherein the visual display device comprises a scanner.

33. The artificial tongue of claim 31 wherein the visual display device comprises a charge-coupled device.

34. The artificial tongue of claim 25 wherein the array is a spatially resolved collection of dyes.

35. The artificial tongue of claim 34 wherein the spatially resolved collection of dyes is a spatially resolved combinatorial family of dyes.

* * * * *

UNITED STATES PATENT AND TRADEMARK OFFICE
CERTIFICATE OF CORRECTION

PATENT NO. : 6,368,558 B1
DATED : October 17, 2002
INVENTOR(S) : Kenneth S. Suslick and Neal A. Rakow It is certified that error appears in the above-identified patent and that said Letters Patent is hereby corrected as shown below:

Column 15,
Line 53, delete the word "way" and substitute therefor -- array --

Signed and Sealed this

Fourth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO.     : 6,368,558 B1
DATED          : April 9, 2002
INVENTOR(S)    : Suslick et al.

It is certified that error appears in the above-identified patent and that said Letters Patent is hereby corrected as shown below:

Column 15,
Line 16, please delete "chlorine" and insert therefor -- chlorin, --

Signed and Sealed this

Fourth Day of January, 2005

JON W. DUDAS
*Director of the United States Patent and Trademark Office*